United States Patent
Schaefer et al.

(10) Patent No.: US 10,254,206 B2
(45) Date of Patent: Apr. 9, 2019

(54) SELF CONTAINED LOAD FRAME FOR IN-SITU INSPECTION

(71) Applicant: The Boeing Company, Chicago, IL (US)

(72) Inventors: Joseph D. Schaefer, St. Louis, MO (US); Roy Martin Gagnon, Summerville, SC (US); Dinu Tandareanu, Charleston, SC (US)

(73) Assignee: THE BOEING COMPANY, Chicago, IL (US)

( * ) Notice: Subject to any disclaimer, the term of this patent is extended or adjusted under 35 U.S.C. 154(b) by 224 days.

(21) Appl. No.: 15/276,962

(22) Filed: Sep. 27, 2016

(65) Prior Publication Data
US 2018/0088013 A1 Mar. 29, 2018

(51) Int. Cl.
*G01N 3/04* (2006.01)
*G01N 3/08* (2006.01)

(52) U.S. Cl.
CPC ............. *G01N 3/08* (2013.01); *G01N 3/04* (2013.01); *G01N 2203/0447* (2013.01); *G01N 2203/0641* (2013.01); *G01N 2203/0658* (2013.01)

(58) Field of Classification Search
CPC .................................. G01N 3/08; G01N 3/04
USPC .......................................................... 73/826
See application file for complete search history.

(56) References Cited

U.S. PATENT DOCUMENTS

| 4,107,982 | A | * | 8/1978 | Mitsui | G01N 3/08 73/571 |
| 4,928,533 | A | * | 5/1990 | Bachelder | G01N 3/08 73/838 |
| 5,798,463 | A | * | 8/1998 | Doudican | G01N 3/08 73/789 |
| 6,142,023 | A | * | 11/2000 | Cole | G01M 5/0058 73/828 |
| 7,770,467 | B1 | * | 8/2010 | Halderman | G01N 3/04 73/849 |
| 9,063,035 | B2 | * | 6/2015 | Kismarton | G01N 3/02 |
| 2009/0007689 | A1 | * | 1/2009 | Kawano | G01N 3/32 73/788 |

(Continued)

FOREIGN PATENT DOCUMENTS

FR 2952717 * 5/2011 ............ G01N 3/08

OTHER PUBLICATIONS

INSTRON, 3300 Series, Affordable Testing Solutions, Jun. 9, 2014, 16 pages.

(Continued)

*Primary Examiner* — John Fitzgerald
*Assistant Examiner* — Jean F Morello
(74) *Attorney, Agent, or Firm* — MH2 Technology Law Group LLP

(57) ABSTRACT

A load frame for applying a tensile load to a test sample during a test or measurement includes a first gripper for gripping a first end of the test sample, a second gripper for gripping a second end of the test sample, and a tensioner for applying the tensile load to the test sample. The load frame further includes a first end tube that encircles the first gripper, a second end tube that encircles the second gripper, and a center tube that encircles a mid-portion of the test sample during the test or measurement. A system such as a wave-generating system may be used to measure the test sample through the center tube during a test or measurement.

20 Claims, 7 Drawing Sheets

(56) References Cited

U.S. PATENT DOCUMENTS

2013/0125661 A1* 5/2013 Arzoumanidis ......... G01B 5/30
73/781

OTHER PUBLICATIONS

INSTRON, 3382, Dual Column Floor Model, May 14, 2015, 2 pages.
INSTRON, 3360 Series, Dual Column Tabletop Models, Sep. 26, 2013, 2 pages.
MTS Acumen Electrodynamic Test Systems, Oct. 12, 2014, 12 pages.

* cited by examiner

US 10,254,206 B2

SELF CONTAINED LOAD FRAME FOR IN-SITU INSPECTION

TECHNICAL FIELD

The present teachings relate to the field of materials metrology and, more particularly, to a device load frame that may be used during the measurement of test sample material characteristics.

BACKGROUND

While this section provides background information related to the present disclosure, the material discussed in this section is not necessarily prior art.

The design and manufacture of a structure requires the selection of appropriate materials for structural components or device substructures. To select a suitable material, scientists, engineers, designers, architects, etc., require specific knowledge of the material such as the internal stress and strain patterns and responses the material exhibits when a force is applied. Various measurement devices have been developed for testing, inspecting, measuring, and quantifying the physical properties of materials that are under load or after loading when no load is applied. Further, the characterization of material properties during loading is known as "in situ" testing or "in situ" inspection. For example, X-rays, acoustic waves, etc., may be used to perform measurements on a sample during the application of a load using computed tomography, radiography, and other well-known inspection techniques.

A test sample may be secured in place during a measurement using a mechanical load frame (i.e., a test fixture) that exerts a load (e.g., tensile force, compressive force, a shear force, or a combination thereof via uniaxial, biaxial, etc., type fixturing) on the test sample. Additionally, thermal or moisture gradients may be applied to a test sample, for example a "coupon," to induce deformation of the coupon by imparting stress/strain gradients to the coupon while it is gripped by and within a load frame. Combinations of thermal and mechanical loadings may also occur. The load frame may include electric motors and/or hydraulics to exert the load on the test sample.

Currently, computed tomography, standard radiography inspection, and other measurement techniques are able to capture constituent (e.g., fiber and matrix) damage modes in composites when a load such as a tensile force is applied to a test sample by a load frame. This is also the case for varieties of composite materials (short fiber, continuous, etc.), thermoplastics, thermosets, additive manufactured materials, metal alloys, etc. Commercially available load frames include benchtop designs as well as larger systems. However, the testing capability of benchtop options is limited, with low load capability (e.g., less than 2 kips) resulting from, for example, small load cell capacity, the size/machine footprint, and at least in part from a limited driving voltage. This low load limitation requires testing of thin test samples which reduces the available range of test sample configurations, material types, and testing conditions. For example, thicker test samples, samples with notches, and samples of various ply layups where the strength exceeds the loading capability are not measurable to the near failure level using these systems because the load level required is beyond the system capability. Larger systems that provide higher load capability may not be portable as they may be fixed in place, and may require extensive and expensive redesign for different sizes and shapes of the test samples. Both benchtop and larger systems have a relatively high cost, and are generally dedicated to only one type of measurement. Switching between measurement techniques, for example, between computed tomography and radiology measurements, as well as measuring a test sample under varying or extreme environmental conditions, is expensive or not possible. Characterization measurements of a material using test samples may be subcontracted to external host sites, but subcontracting may be expensive and requires long initial lead times and increased time to complete testing.

A load frame that is portable, simply reconfigurable and adjustable for various test sample (i.e., coupon) sizes, and able to integrate with different types of metrology systems, such as computed tomography, acoustic emission, and radiology systems, would be a welcome addition to the art.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In an embodiment, a load frame may include a first gripper configured to position a first end of a test sample, a second gripper configured to position a second end of the test sample, and a center tube that encircles a test region. The test region may be disposed between the first gripper and the second gripper and the center tube may be configured to allow passage of a penetrating wave through the center tube to the test region. The load frame may further include a first end tube that encircles the first gripper and is axially aligned with the center tube, and a second end tube that encircles the second gripper and is axially aligned with the center tube and the first end tube. The center tube may be positioned between the first end tube and the second end tube. The first end tube may be a first cylinder, the second end tube may be a second cylinder, and the center tube may be a third cylinder.

In an embodiment, the load frame may further include a first tube cap that physically contacts the first end tube and the center tube and a second tube cap that physically contact the second end tube and the center tube. The first tube cap may a first slot configured to receive the test sample and the second tube cap may define a second slot configured to receive the test sample. The load frame may further include a first end cap that physically contacts the first end tube and a second end cap that physically contacts the second end tube. In an embodiment, a tensioner is configured to apply a compressive force to the first end tube, the second end tube, and the center tube, and is further configured to applied a tensile load to the test sample. The tensioner may include a jack bolt extending through a hole in the second end cap and at least one external nut attached to the jack bolt, wherein the tensile load applied to the test sample is configured to be adjusted through manual rotation of the external nut. The tensioner may be attached to the second gripper and configured to move the second gripper toward and away from the first gripper during rotation of the external nut.

Optionally, the tensioner may further include a midplate positioned between the second gripper and the second end cap. The midplate may include a central opening therein with the jack bolt extending through the central opening in the midplate. In an embodiment, at least one clevis pin extends through the second end cap and through the midplate and is configured to reduce or prevent torsional stresses in the test sample during rotation of the external nut.

The load frame may optionally include an adapter attached to the midplate and to the second gripper, and a tension plate attached to the first gripper and having a bottom surface. The second end cap may include a flat edge that rests on the bottom surface of the tension plate and slides along the bottom surface during rotation of the external nut.

A test sample may include a first end, a second end, and a mid-portion between the first end and the second end. In an embodiment, the first gripper positions the first end, the second gripper positions the second end, and the center tube encircles the mid-portion. The first gripper may be a first clamp including a first pair of opposing jaws, and the second gripper may be a second clamp including a second pair of opposing jaws.

In another embodiment, a method for performing a test, measurement, and/or inspection on a test sample may include securing a first end of the test sample within a first gripper, placing a first end tube over the first gripper such that the first end tube encircles the first gripper, inserting a second end of the test sample through a first slot in a first tube cap, and positioning the first tube cap onto the first end tube. The method may further include inserting the second end of the test sample into a center tube, physically contacting the center tube with the first tube cap, inserting the second end of the test sample through a second slot in a second tube cap, and physically contacting the second tube cap onto the center tube. The second end of the test sample may be secured within a second gripper, and a second end tube may be placed over the second gripper such that the second end tube encircles the second gripper. A tensile load may be exerted on the test sample using a tensioner while a mid-portion of the test sample is positioned within the center tube. In an embodiment, the first gripper secures the first end of the test sample and the second gripper secures the second end of the test sample.

The method may further include exerting a compressive force on the first end tube, the second end tube, and the center tube during the exerting of the tensile load on the test sample. An external nut on a jack bolt may be rotated to increase the tensile load on the test sample. Additionally, the second gripper may be attached to the tensioner subsequent to the securing of the second end of the test sample within the second gripper and prior to the exerting of the tensile load on the test sample. The first end tube, the second end tube, and the center tube may be cylinders, and the method may further include axially aligning the first end tube, the second end tube, and the center tube, each with the other.

BRIEF DESCRIPTION OF THE DRAWINGS

The accompanying drawings, which are incorporated in, and constitute a part of this specification, illustrate embodiments of the present teachings and, together with the description, serve to explain the principles of the disclosure. In the figures.

It should be noted that some details of the FIGS. have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same or like parts.

The present teachings provide a method and structure for testing and/or obtaining performance data from a test sample. The structure includes a load frame (i.e., test fixture) that exerts a force, such as a tensile force, on a test sample (i.e., coupon). In various implementations, the load frame may be a mechanical load frame that includes no electric motors or hydraulics, thereby reducing initial cost as well as the maintenance cost of the load frame. In an embodiment, the force applied to the test sample may be manually set and adjusted by an operator. The load frame may be relatively light in weight and portable. Further, in an embodiment, the load frame may have the capability to exert a wide range of forces onto the test sample, for example, from about 0 kips to about 12 kips or larger depending on the configuration of device components.

Figure 1:
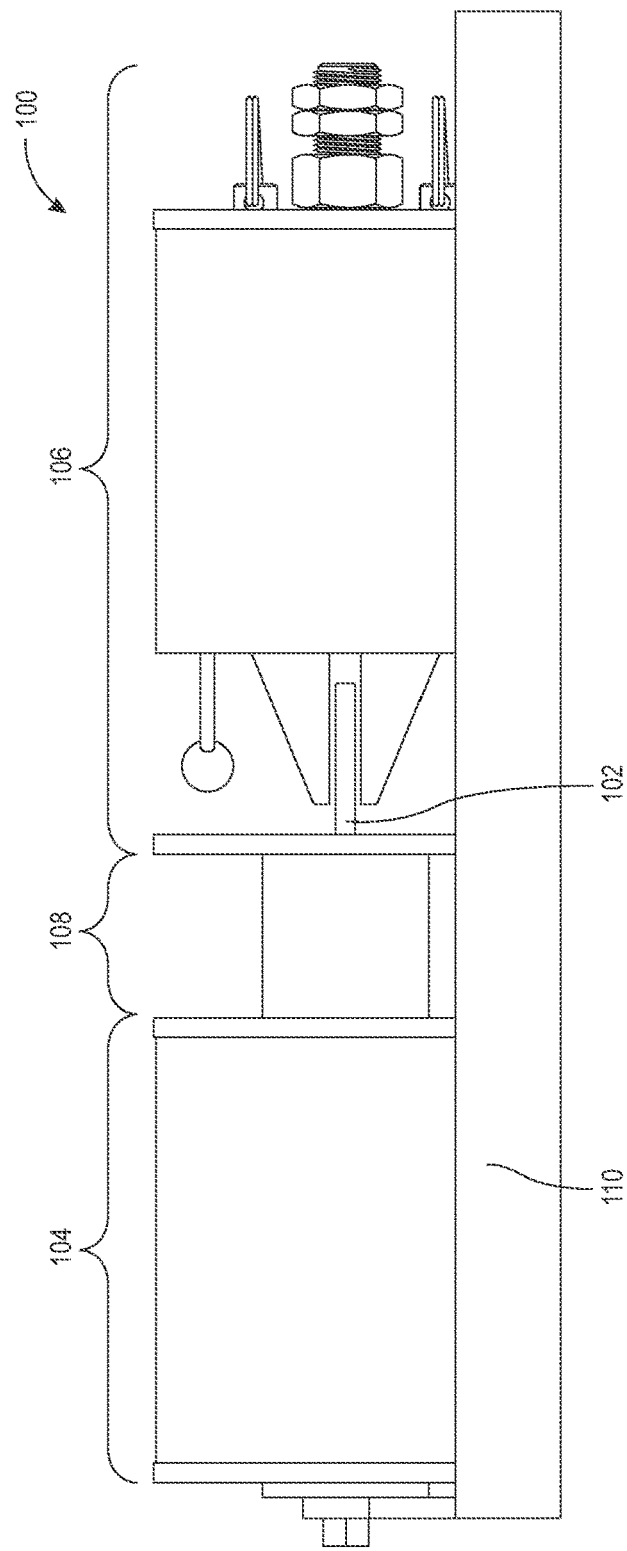
FIG. 1 is a side perspective depiction of a load frame in accordance with an embodiment of the present teachings.

A load frame 100 according to one embodiment of the present teachings is depicted in the side view of FIG. 1. The load frame 100 may be used to maintain a position of, and load on, a test sample 102 during a test or measurement. For purposes of description, the load frame 100 in the FIG. 1 embodiment may be generally described as including a first grip assembly 104 that maintains the position of a first end of the test sample 102, a second grip assembly 106 that maintains the position of a second end of the test sample 102 and may be adjusted to exert a desired force on the sample 102, and a test region 108 where a measurement of the test sample under stress is performed. In FIG. 1, the second grip assembly 106 is depicted in a retracted position to show the test sample 102. The load frame 100 may further include a tension plate 110. Each of these substructures is described in detail below. It will be understood that the FIGS. are generalized schematic depictions and that an actual structure in accordance with an embodiment may include other substructures that are not depicted for simplicity, while various depicted substructures may be removed or modified.

Figure 2:
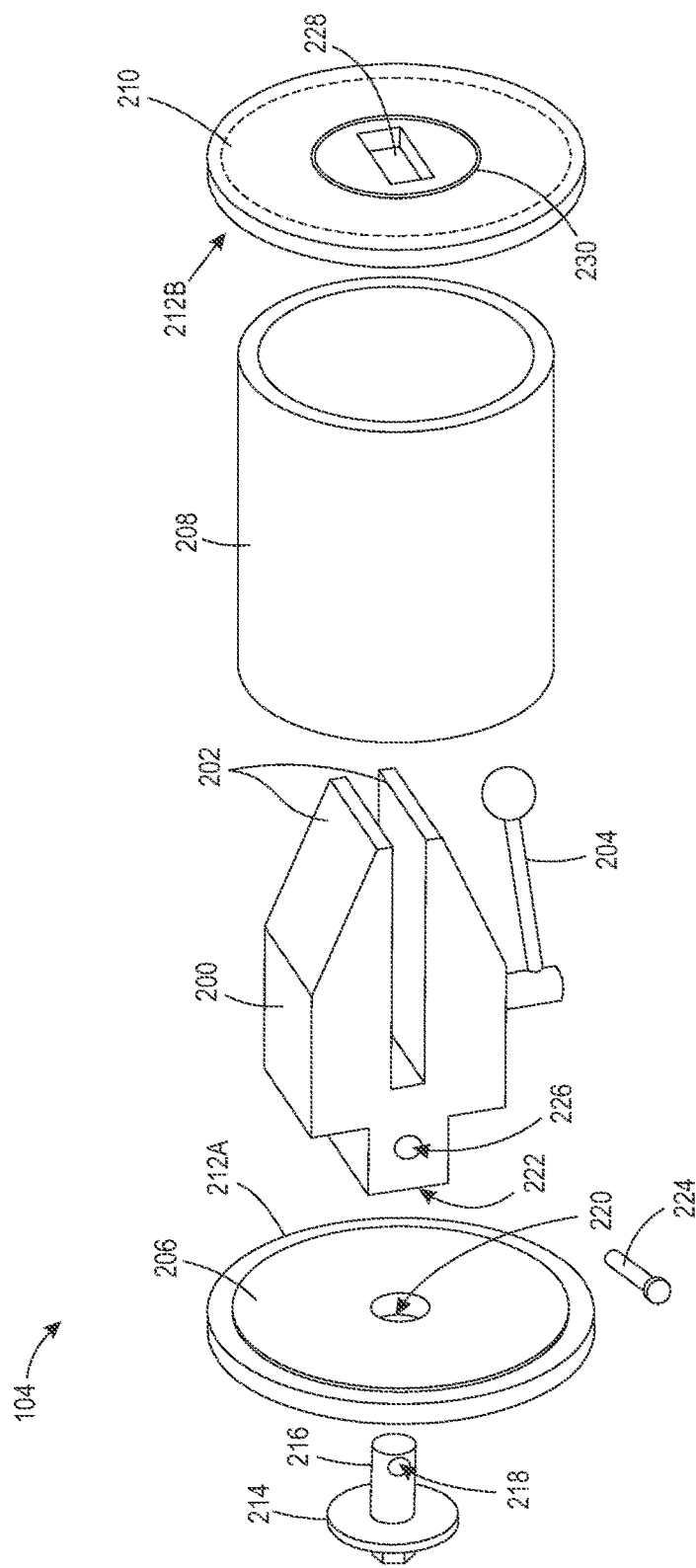
FIG. 2 is an exploded perspective depiction of a first grip assembly in accordance with the load frame of FIG. 1.

FIG. 2 is an exploded perspective depiction of the first grip assembly 104, which may include a first gripper 200 that secures and positions the first end of the test sample 102. While the grippers are depicted herein and described with reference to clamps, it will be appreciated that other grippers, such as spring-loaded clips or other clips, binders, pins, etc., are contemplated. The first clamp 200 may include a pair of opposing jaws 202 and a handle 204 or other mechanism to aid with securing the test sample 102 (FIG. 1) within the gripper 200 during a measurement. In the depicted embodiment, the handle 204 may be rotated to move one or both of the opposing jaws 202. FIG. 2 further depicts a first end cap 206, a first end tube 208, and a first tube cap 210. The first end cap 206 and the first tube cap 210 may define first end tube channels 212A, 212B respectively for receiving and positioning opposite ends of the first end tube 208.

FIG. 2 further depicts a first adapter 214 including a first adapter pin 216 having a hole 218 therethrough that mounts the first clamp 200 to the first end cap 206. The first adapter pin 216 may be inserted into a hole 220 through the first end cap 206, and into a first mounting hole 222 that extends at least partially through a surface of the first clamp 200. A locking pin 224 may be inserted into a second mounting hole 226 and through the hole 218 in the first adapter pin 216 to fasten the first clamp 200 to the first end cap 206. During use, the first end tube 208 may encircle the first clamp 200 while the first clamp 200 positions and secures a first end of the test sample 102. During a measurement, the test sample 102 may extend through a first slot 228 through the first tube cap 210, for example, as described below with reference to FIG. 6.

Figure 3:
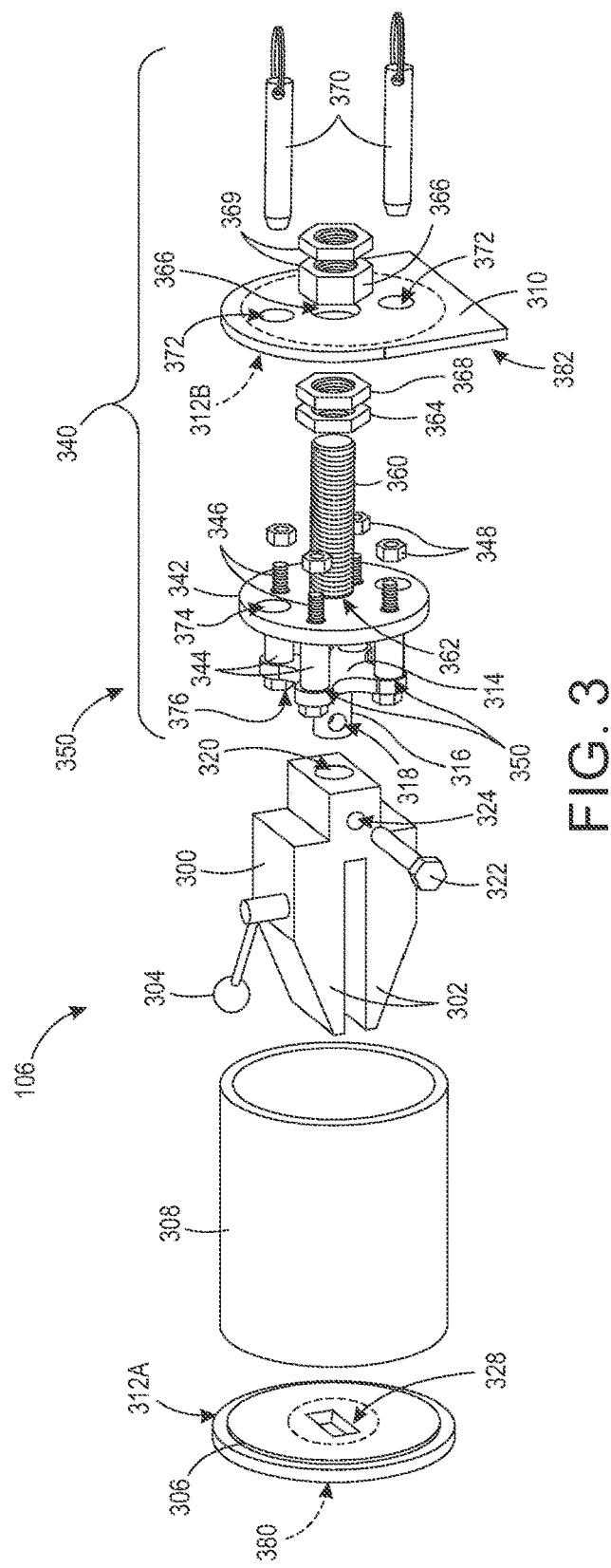
FIG. 3 is an exploded perspective depiction of a second grip assembly including a tensioner in accordance with the load frame of FIG. 1.

FIG. 3 is an exploded perspective depiction of the second grip assembly 106, which may include a second gripper 300 that secures and positions the second end of the test sample 102. The second gripper 300 may be a second clamp 300 of a same or different design than the first clamp 200. The second clamp 300 may include a pair of opposing jaws 302 and a handle 304 or other mechanism to aid with securing the test sample 102 within the first clamp 200 during a measurement. In the depicted embodiment, the handle 304 may be rotated to move one or both of the jaws 302. FIG. 3 further depicts a second tube cap 306, a second end tube 308, and a second end cap 310. The second tube cap 306 and the second end cap 310 may define second end tube channels 312A, 312B respectively for receiving and positioning opposite ends of the second end tube 308.

FIG. 3 further depicts a second adapter 314 including a second adapter pin 316 having a hole 318 therethrough that mounts the second clamp 300 to the second adapter 314. The second adapter pin 316 may be inserted into a third mounting hole 320 that extends at least partially through a surface of the second clamp 300. A locking pin 322 may be inserted into a fourth mounting hole 324 in the second clamp 300 and through the hole 318 in the second adapter pin 316 to fasten the second clamp 300 to the second adapter 314. During use, the second end tube 308 may encircle the second clamp 300 while the second clamp 300 positions and secures the second end of the test sample 102. The test sample 102 may extend through a second slot 328 through the second tube cap 306, for example, as described below with reference to FIG. 6.

FIG. 3 further depicts a tensioner 340 that may be used to adjust a force placed on the test sample 102 prior to testing. It will be appreciated that other tensioner designs and structures are contemplated. The tensioner 340 includes a midplate 342 and a plurality of spacers 344 that may attached between the second adapter 314 and the midplate 342 using, for example, a plurality of bolts 346 and nuts 348. In an embodiment, the each bolts 346 may be inserted through one hole 350 of a plurality of holes in the second adapter 314, through one of the spacers 344, through one hole 352 of a plurality of holes in the midplate 342, and secured with one of the nuts 348, for example, as depicted in the assembled view of FIG. 6.

The tensioner 340 further includes a jack bolt 360 that extends through a central opening 362 through the midplate 342, and one or more nuts 364 that secures the jack bolt 360 to the midplate 342. The jack bolt 360 further extends through and protrudes from an opening 366 in the second end cap 310, and is adjustably mounted to the second end cap 310 using, for example, one or more internal nuts 368 and external nuts 369. Rotation of the midplate 342, and thus the second clamp 300 and the test sample 102, may reduced or prevented during a force adjustment using, for example, one or more clevis pins 370 that extend through one or more holes 372 in the second end cap 310, through one or more clevis pin holes 374 in the midplate 342, and into one or more contours or holes 376 in the second adapter 314 (see also the assembled perspective depiction of FIG. 6). Maintaining alignment of the first clamp 200, the second clamp 300, and the test sample 102 during the application of the tensile load protects the test sample from experiencing out-of-plane loading.

Figure 4:
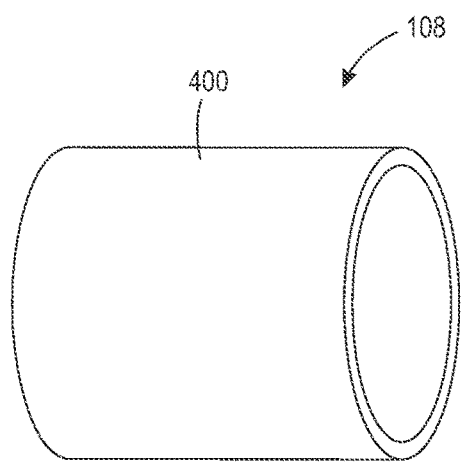
FIG. 4 is a perspective depiction of a center tube in accordance with the FIG. 1 embodiment.

FIG. 4 is a perspective depiction of the test region 108 that includes a center tube 400. During a measurement, a first end of the center tube 400 may be received by a center tube channel 230 (FIG. 2) within the first tube cap 210, and a second end of the center tube 400 may be received by a center tube channel 380 (FIG. 3) within the second tube cap 306. Center tube channels 230, 380 may assist in positioning the first and second ends of the center tube 400. During use, the center tube 400 may encircle a mid-portion of the test sample 102, wherein the mid-portion is between the first and second ends of the test sample.

Figure 5:
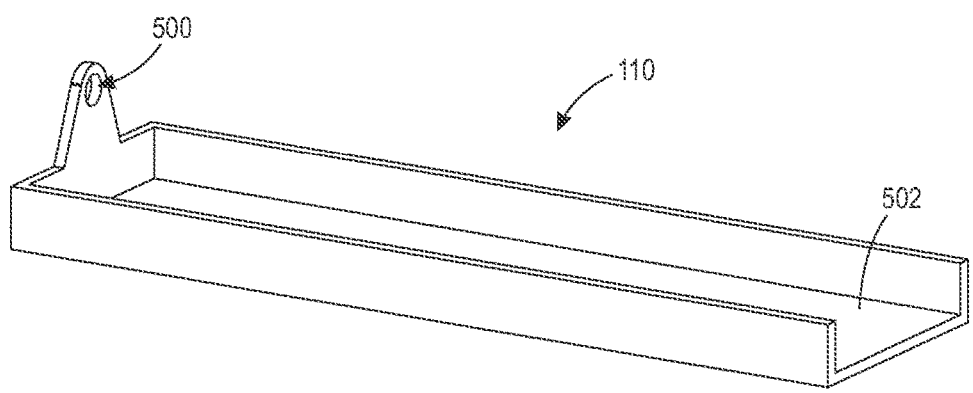
FIG. 5 is a perspective depiction of a tension tray in accordance with the load frame of FIG. 1.

FIG. 5 is a perspective depiction of the tension plate 110. During placement of the test sample 102 within the load frame 100 and testing of the test sample 102, the tension plate 110 may stabilize the structures of FIGS. 2-4. The tension plate 110 may further mitigate transport of the load frame 100 from, for example, an assembly location to a testing location. The first adapter pin 216 of the first adapter 214 may be inserted through a hole 500 within the tension plate 110 prior to insertion into the first mounting hole 222 in the first clamp 200, thereby securing the first grip assembly 104 to the tension plate 110. During adjustment of the force applied to the test sample 102 using the tensioner 340, a flat edge 382 (FIG. 3) of the second end cap 310 may rest on, and slide along, a bottom surface 502 of the tension plate 110.

Figure 6:
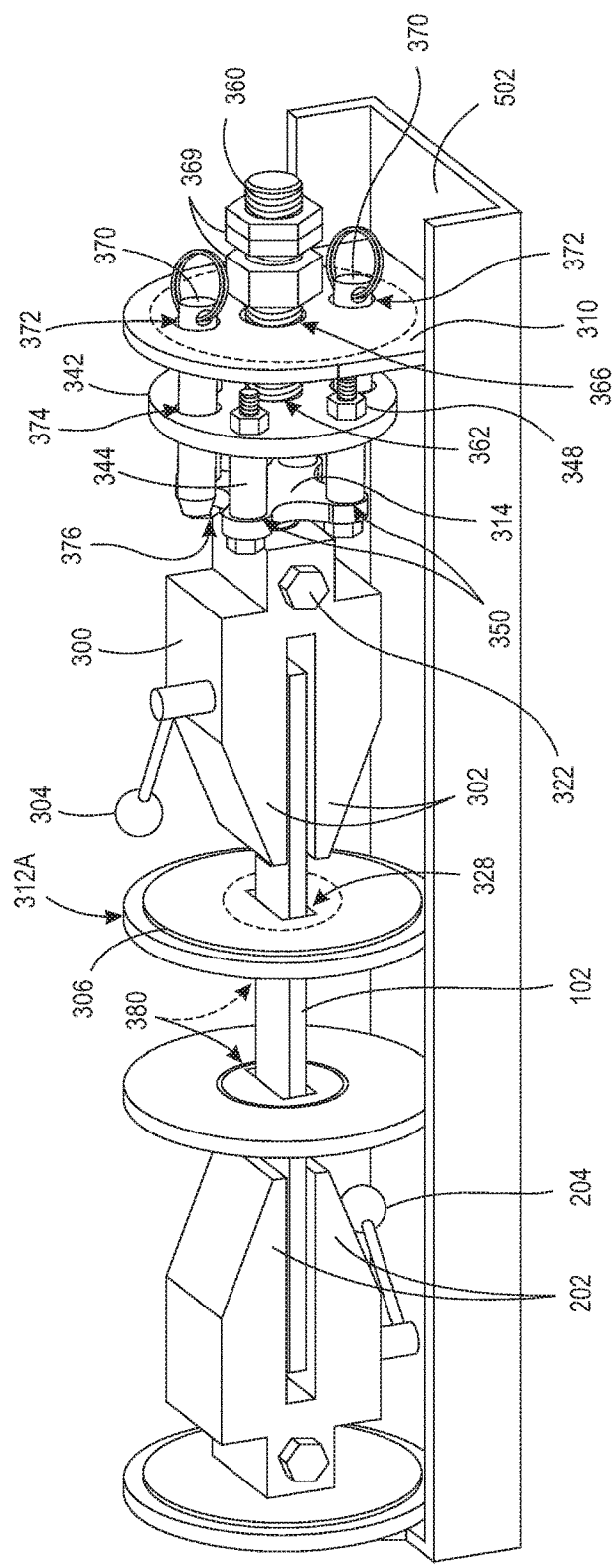
FIG. 6 is an assembled perspective depiction of the FIG. 1 load frame with various tubes hidden to reveal internal structures.
Figure 7:
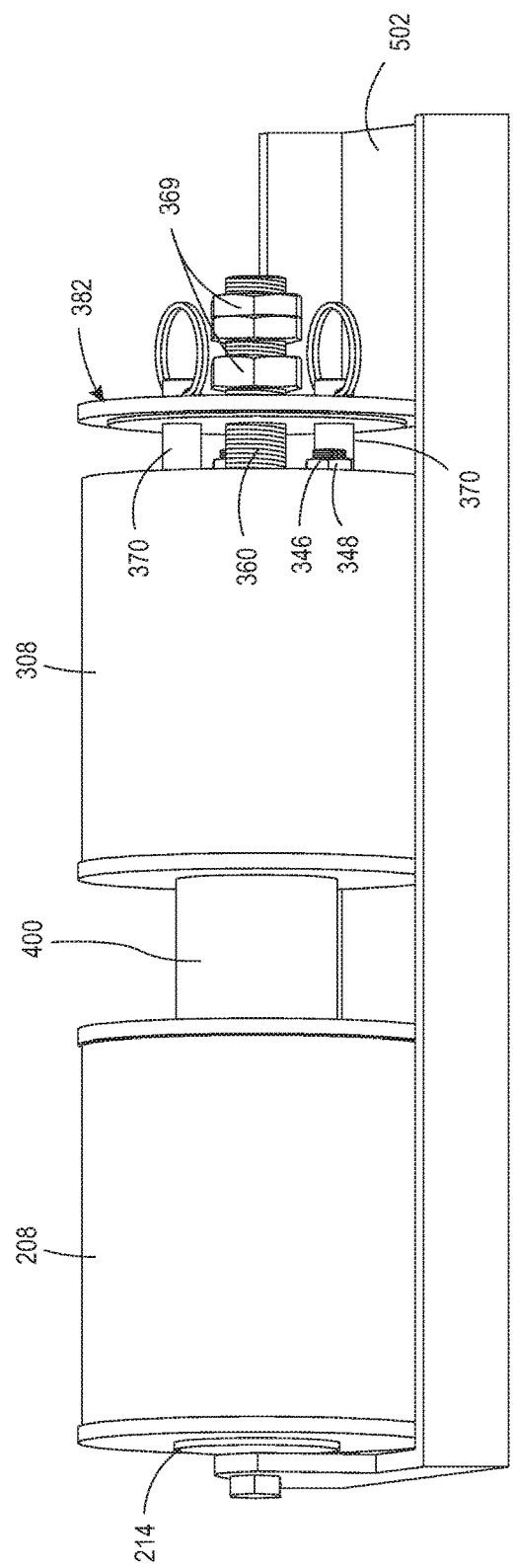
FIG. 7 is an assembled perspective depiction of the FIG. 1 load frame.

FIG. 6 is a perspective depiction of the test sample 102 positioned within the load frame 100 and ready for a test or measurement. In FIG. 6, the first end tube 208 (FIG. 2), the second end tube 308 (FIG. 3), and the center tube 400 (FIG. 4) have been hidden to depict the internal structure of the load frame 100, while these structures are depicted in the perspective depiction of FIG. 7. While the first end tube 208, the second end tube 308, and the center tube 400 are configured as being axially aligned cylinders, other shapes are contemplated.

Figure 8:
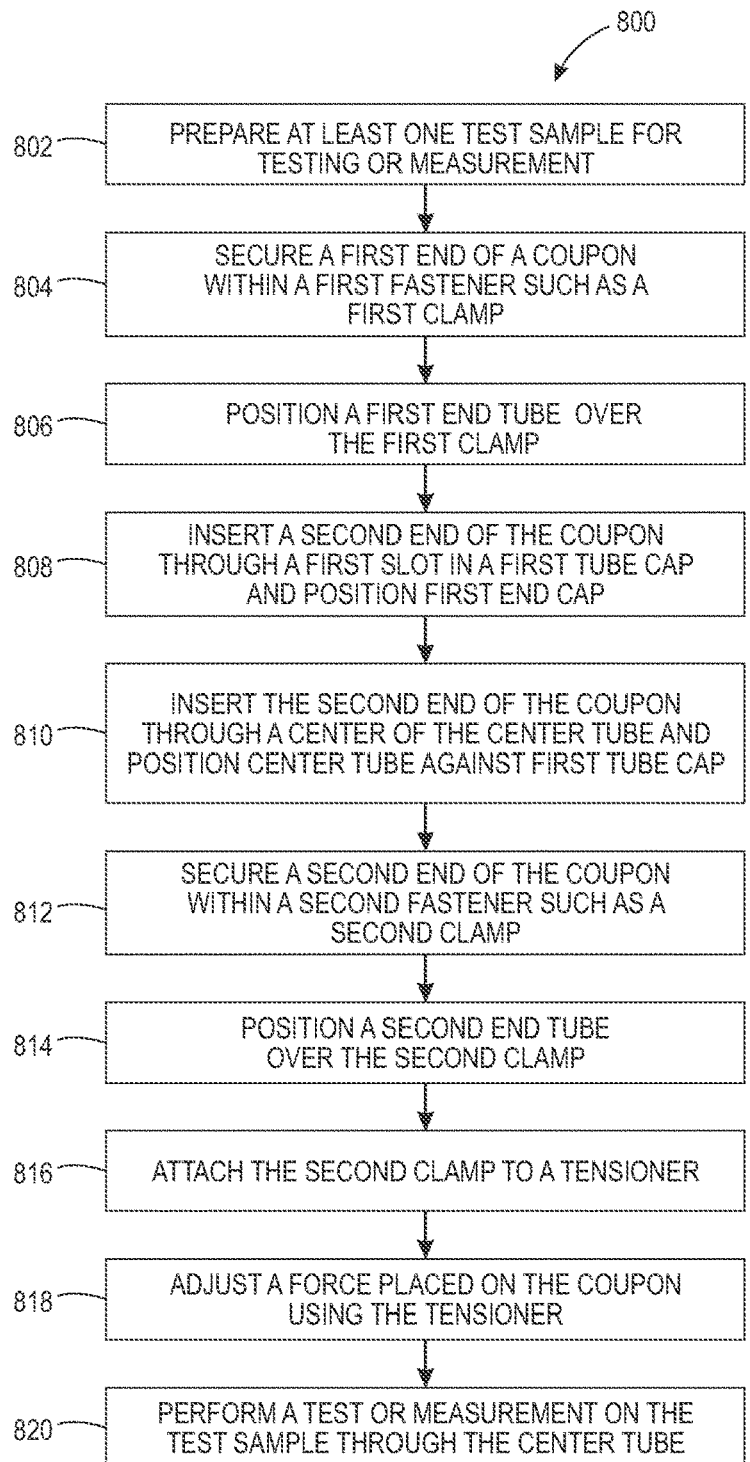
FIG. 8 is a flow chart showing a method for testing or measuring a test sample in accordance with an embodiment of the present teachings.

A method for performing a test or measurement 800 on a test sample 102 will now be described with reference to FIGS. 1-7 and the flow chart of FIG. 8. Prior to performing the following process acts, it is assumed that the load frame 100 is in a ready state by partial assembly of the load frame 100. For example, the first clamp 200 and the first end cap 206 may be pre-attached to the tension plate 110 using the first adapter 214 and the locking pin 224. Further, some of the subassemblies of the second grip assembly 106 may be assembled as described above and therefore in a ready state.

For example, the tensioner 340 may be assembled, and the second clamp 300 may be detached from the second adapter 314.

At 802, at least one test sample (e.g., coupon) 102 is prepared. The test sample may be, for example, a carbon fiber reinforced polymer, another polymer or synthetic composite, a metal or metal alloy, or another material. The size, shape, and thickness of the test sample 102 is at least partly dependent on the component size and load capacity of the load frame 100. In an embodiment, a coupon may be from about 0.25 inches to about 1.5 inches wide, from about 1.0 inch to about 10 inches long, and from about 0.01 inches to about 0.25 inches thick, or another suitable thickness.

Next, as depicted at 804, the first end of the test sample 102 may be secured within the first gripper 200, such as the first clamp 200, for example, by positioning the first end between the opposing jaws 202 of the first clamp 200 and tightening the jaws 202 using the handle 204 to secure the first end of the test sample 102.

Subsequently, at 806, the first end tube 208 may be placed over the first clamp 200 such that a first end of the first end tube 208 physically contacts the first end cap 206 and the first end tube encircles the first clamp. A first lip of first end tube 208 may be positioned by and within the first end tube channel 212A of the first end cap 206. Next, at 808, a second end of the coupon is inserted through the first slot 228 in the first tube cap 210, and the first tube cap 210 is positioned onto the first end tube 208. A second lip of the first end tube 208 may be positioned by and within the first end tube channel 212B of the first tube cap 210.

Subsequently, the second end of the coupon 102 may be inserted into center tube 400 and a first lip of the center tube 400 may be positioned by and within the center tube channel 230 of the first tube cap 210 as shown at 810 such that the center tube physically contacts the first tube cap.

Next, at 812, the second end of the test sample 102 may be inserted through the second slot 328 in the second tube cap 306 and the second end of the test sample 102 may be secured within the second gripper 300, for example, by physically contacting the second tube cap 306 with center tube 400, positioning the second end between the opposing jaws 302 of the second clamp 300, and tightening the jaws 302 using the handle 304 to secure the second end of the test sample 102.

At 814, the second end tube 308 may be placed over the second clamp 300 such that a first end of the second end tube 308 physically contacts the second tube cap 306. A first lip of second end tube 308 may be positioned by and within the second end tube channel 312A of the second tube cap 306. Next, at 816, the second clamp 300 is physically attached to the tensioner 340, for example, by inserting the second adapter pin 316 into the third mounting hole 320, then inserting the locking pin 322 into the fourth mounting hole 324 and the hole 318 in the second adapter pin 316.

Next, the load frame 100 may be tightened, for example, such that a second lip of the second end tube 308 is positioned by and within the second end tube channel 312B of the second end cap 310. The load frame 100 may be tightened and adjusted manually, for example, by clockwise rotation of the one or more external nuts 369 at the end of the jack bolt 360 that protrudes from the second end cap 310. Continued clockwise rotation of the one or more external nuts 369 on the jack bolt 360 results in the application of a compressive force which may be uniformly distributed around a circumference of various substructures of the load frame 100 including, for example, the first end tube 208, the center tube 400, and the second end tube 308. As this compressive force increases, the second clamp 300 moves away from the first clamp 200 and slack on the test sample 102 is removed and a tensile force begins to be applied to the test sample 102. Further clockwise rotation of the one or more external nuts 369 results in an increased tensile force placed on the test sample 102. The load frame 100 may be integrated or combined with a strain gauge (not individually depicted for simplicity) such that a desired tensile force may be measured and applied to the test sample during a test or measurement.

During tightening of the external nuts 369, the clevis pins 370 that extend through the one or more holes 372 in the second end cap 310, through one or more clevis pin holes 374 in the midplate 342, and into one or more contours or holes 376 in the second adapter 314 may reduce or prevent axial rotation of the test sample 102. This undesired axial rotation may otherwise place undesired torsional stresses on the test sample 102 and result in inaccurate test results.

After applying a desired tensile force to the test sample, a test or measurement may be performed as shown at 820. The test or measurement of the test sample 102 may be performed through the center tube 400 using, for example, a penetrating wave such as an X-ray, an ultrasonic wave, a radio wave, etc., or another desired measurement technique. The structural integrity of the center tube 400 to resist and withstand the compressive forces applied during compression and transport may therefore be balanced with the ability of the measurement technique to penetrate the center tube 400 to measure stress characteristics of the test sample 102. Thus the center tube 400 is designed to allow a suitable transmission of the penetrating wave through the center tube 400 to impart the penetrating wave to the test sample 102 and return the wave data to a data collector, which may also be the wave generator or another data collector. In an embodiment, the center tube 400 may be manufactured from a metal such as aluminum or an aluminum alloy, for example 6061 aluminum alloy, a steel alloy such as a 304 steel alloy or a 316 steel alloy, another metal alloy or metal, or a synthetic material such as a polymer or a natural material such as quartz. In an embodiment, the center tube 400 may be a 6061 aluminum alloy having a thickness of from about 0.049 inches to about 0.125 inches, or from about 0.06 inches to about 0.10 inches, or from about 0.06 inches to about 0.07 inches, for example 0.065 inches. The center tube 400 may have an outside diameter that depends, at least in part, on the dimensions of the test sample 102. In an embodiment, the center tube may have an outside diameter of from about 0.25 inches to about 6.0 inches, or from about 1.0 inches to about 3.0 inches, for example about 2.0 inches.

Settings of test equipment (not individually depicted for simplicity) during a measurement will depend at least in part on, for example, the type and design of measurement system used to generate the test wave, the dimensions and composition of the center tube, as well as other considerations that can be determined by an artisan in the art.

Note that while the exemplary method is illustrated and described above as a series of acts or events, it will be appreciated that the present embodiments are not limited by the illustrated ordering of such acts or events. For example, some acts may occur in different orders and/or concurrently with other acts or events apart from those illustrated and/or described herein, in accordance with the present teachings. In addition, not all illustrated steps may be required to implement a methodology in accordance with the present teachings, and other steps can be added or modified.

It will be appreciated that a load frame according to the description herein may provide an inexpensive, lightweight, and portable test fixture. The test sample may be prepared at one location and then transported to another location such as an environmentally controlled chamber (i.e., thermally controlled, pressure controlled, atmospheric controlled, etc.) or a test station that includes a non-mobile wave generating system. The load frame may be integrated with many different wave generating systems such as different computed tomography platforms, and the compact design allows the test fixture to be inspected with other non-destructive evaluation techniques such as radiography and acoustic emission sensing. The modular design may better allow for coupons of various lengths to be evaluated, in contrast to systems that can test only coupons having one size. For example, clamps 200, 300 having different lengths, gripping, and/or loading capacities can be quickly and easily exchanged. Additionally, the length of the center tube may be increased or extended to provide an increased regions of interest for scanning larger coupon areas. The application of the load to the test sample may be a manual adjustment and therefore requires no electric or hydraulic system support or special equipment to operate. The load frame is relatively simple to operate and thus training time for technicians or other operating personnel is low.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:

1. A load frame, comprising:
a first gripper configured to position a first end of a test sample;
a second gripper configured to position a second end of the test sample;
a center tube that encircles a test region;
a first end tube that encircles the first gripper and is axially aligned with the center tube; and
a second end tube that encircles the second gripper and is axially aligned with the center tube and the first end tube,
wherein:
the center tube is positioned between the first end tube and the second end tube;
the test region is disposed between the first gripper and the second gripper; and
the center tube is configured to allow passage of a penetrating wave through the center tube to the test region.

2. The load frame of claim 1, wherein the first end tube is a first cylinder, the second end tube is a second cylinder, and the center tube is a third cylinder.

3. The load frame of claim 2, further comprising:
a first tube cap that physically contacts the first end tube and the center tube; and
a second tube cap that physically contacts the second end tube and the center tube.

4. The load frame of claim 3, wherein:
the first tube cap defines a first slot configured to receive the test sample; and
the second tube cap defines a second slot configured to receive the test sample.

5. The load frame of claim 4, further comprising:
a first end cap that physically contacts the first end tube; and
a second end cap that physically contacts the second end tube.

6. The load frame of claim 5, further comprising a tensioner configured to apply a compressive force to the first end tube, the second end tube, and the center tube, and further configured to applied a tensile load to the test sample.

7. The load frame of claim 6, wherein the tensioner comprises a jack bolt extending through a hole in the second end cap and at least one external nut attached to the jack bolt, wherein the tensile load applied to the test sample is configured to be adjusted through manual rotation of the external nut.

8. The load frame of claim 7, wherein the tensioner is attached to the second gripper and is configured to move the second gripper toward and away from the first gripper during rotation of the external nut.

9. The load frame of claim 8, wherein:
the tensioner further comprises a midplate positioned between the second gripper and the second end cap;
the midplate comprises a central opening therein; and
the jack bolt extends through the central opening in the midplate.

10. The load frame of claim 9, further comprising at least one clevis pin that extends through the second end cap and through the midplate, wherein the at least one clevis pin is configured to reduce or prevent torsional stresses in the test sample during rotation of the external nut.

11. The load frame of claim 10, further comprising an adapter attached to the midplate and to the second gripper.

12. The load frame of claim 11, further comprising a tension plate attached to the first gripper and having a bottom surface, wherein the second end cap comprises a flat edge that rests on the bottom surface of the tension plate and is configured to slide along the bottom surface during rotation of the external nut.

13. The load frame of claim 11, further comprising a test sample having a first end, a second end, and a mid-portion between the first end and the second end, wherein the first gripper positions the first end, the second gripper positions the second end, and the center tube encircles the midportion.

14. The load frame of claim 1, wherein the first gripper is a first clamp comprising a first pair of opposing jaws, and the second gripper is a second clamp comprising a second pair of opposing jaws.

15. A method for performing a test, measurement, and/or inspection on a test sample, comprising:
securing a first end of the test sample within a first gripper;
placing a first end tube over the first gripper such that the first end tube encircles the first gripper;
inserting a second end of the test sample through a first slot in a first tube cap;
positioning the first tube cap onto the first end tube;
inserting the second end of the test sample into a center tube;
physically contacting the center tube with the first tube cap;
inserting the second end of the test sample through a second slot in a second tube cap;
physically contacting the second tube cap with the center tube;
securing the second end of the test sample within a second gripper;
placing a second end tube over the second gripper such that the second end tube encircles the second gripper; and
exerting a tensile load on the test sample using a tensioner while a mid-portion of the test sample is positioned within the center tube, the first gripper secures the first end of the test sample, and the second gripper secures the second end of the test sample.

16. The method of claim 15, further comprising exerting a compressive force on the first end tube, the second end tube, and the center tube during the exerting of the tensile load on the test sample.

17. The method of claim 16, further comprising rotating an external nut on a jack bolt to increase the tensile load on the test sample.

18. The method of claim 17, further comprising attaching the second gripper to the tensioner subsequent to the securing of the second end of the test sample within the second gripper and prior to the exerting of the tensile load on the test sample.

19. The method of claim 18, wherein the first end tube, the second end tube, and the center tube are cylinders, and the method further comprises axially aligning the first end tube, the second end tube, and the center tube, each with the other.

20. A load frame, comprising:
a first gripper configured to position a first end of a test sample;
a second gripper configured to position a second end of the test sample;
a test region positioned between the first gripper and the second gripper;
a center tube that encircles the test region;
a first end tube that encircles the first gripper; and
a second end tube that encircles the second gripper,
wherein:
the center tube is positioned between the first end tube and the second end tube; and
the center tube is configured to allow passage of a penetrating wave through the center tube to the test region.

* * * * *